United States Patent [19]

Nakamura et al.

[11]  4,105,656

[45]  Aug. 8, 1978

[54] PROCESS FOR PREPARING 3-N-MONOSUBSTITUTED AMINO-4-SUBSTITUTED-5-PYRAZOLONES

[75] Inventors: Kotaro Nakamura; Seiji Ichijima; Nobuo Furutachi; Yosio Kosuge, all of Minami-ashigara, Japan

[73] Assignee: Fuji Photo Film Co., Ltd., Minami-ashigara, Japan

[21] Appl. No.: 764,481

[22] Filed: Jan. 31, 1977

[30] Foreign Application Priority Data

Jan. 30, 1976 [JP] Japan ..................................... 51-8988

[51] Int. Cl.² ............................................. C07D 231/16
[52] U.S. Cl. ................................. 260/239.9; 544/270; 544/277; 544/316; 544/319; 544/276; 544/328; 544/238; 544/237; 260/295 L; 260/305; 260/308 R; 260/308 B; 548/327; 548/327; 548/336; 548/359; 548/360
[58] Field of Search ........... 260/308 B, 308 R, 295 L, 260/305, 239.9, 251 A, 256.4 N, 250 BN, 250 P, 252, 254, 256, 256.4 F; 548/327, 360, 336, 359

[56] References Cited

U.S. PATENT DOCUMENTS

| | | | |
|---|---|---|---|
| 3,935,262 | 1/1976 | Lestina | 260/559 R |
| 3,956,339 | 5/1976 | Furutachi | 260/295 R |

Primary Examiner—Cecilia M. Jaisle
Attorney, Agent, or Firm—Sughrue, Rothwell, Mion, Zinn and MacPeak

[57] ABSTRACT

A process for preparing a 3-N-mono-substituted amino-4-substituted-5-pyrazolone which comprises replacing the hydrogen atom of the NH group at the 3-position of a 3-mono-substituted-5-pyrazolone with a protective group, halogenating the resulting compound to introduce a halogen atom into the 4-position, reacting the resulting compound with a 5- or 6-member heterocyclic compound containing two or more nitrogen atoms to replace the halogen atom at the 4-position with a nitrogen containing heterocyclic group, and hydrolyzing the resulting compound to remove the protective group.

5 Claims, No Drawings

PROCESS FOR PREPARING 3-N-MONOSUBSTITUTED AMINO-4-SUBSTITUTED-5-PYRAZOLONES

BACKGROUND OF THE INVENTION

1. Field of the Invention

The present invention relates to a process for preparing 4-substituted-5-pyrazolones from 3-alkylamino-5-pyrazolones, 3-arylamino-5-pyrazolones or 3-N-heterocyclic (substituted) amino-5-pyrazolones as starting materials.

2. Description of the Prior Art

It is well known that 5-pyrazolones are important compounds as magenta couplers in the field of photography and that they are useful materials as intermediates for synthesizing medicines or dyestuffs. For example, in the field of photography, when conventional silver halide emulsion type color photographic sensitive materials containing 5-pyrazolones are subjected to color development after exposure to light, the 5-pyrazolones function as couplers and form corresponding azomethine dyes by oxidative coupling with p-phenylenediamine type color developing agents to form magenta images.

It is also well known that 4-unsubsituted-5-pyrazolone couplers stoichiometrically require 4-equivalents of silver halide as an oxidizing agent, because one molecule of the coupler forms one molecule of azomethine dye by an oxidative coupling reaction. On the contrary, 5-pyrazolones having a substituent at the 4-position which is easily released at coupling stoichiometrically require only 2 equivalents of silver halide for forming dyes. Various kinds of releasable groups on the 4-position of such pyrazolone couplers are known. They are, for example, described in U.S. Pat. Nos. 3,253,924, 3,311,476, 3,419,391, 3,522,051 and 2,434,272. Pyrazolone couplers which exhibit a development inhibiting effect around the periphery of the image areas due to the interaction of a group released at coupling with silver halide adjacent to this group are also known. Namely, these kinds of 4-substituted 5-pyrazolones are 2-equivalent couplers which release a development inhibitor (DIR Coupler), and are described in, for example, U.S. Pat. Nos. 3,227,554, 3,701,783, 3,148,062, 3,617,291 and 3,006,759.

Further, 3-alkylamino-5-pyrazolone type couplers, 3-arylamino-5-pyrazolone type couplers and 3-N-heterocyclic amino 5-pyrazolone type couplers have excellent color forming properties, excellent color fastness and excellent color hue (for example, as described in U.S. Pat. No. 2,311,081 (U.S. Reissue Pat. No. 22,329)).

It is understood from the above descriptions that 3-N-substituted amino-5-pyrazolones having a releasable substituent at the 4-position are very important compounds in the preparation of color photographic sensitive materials.

Processes for preparing 4-substituted-5-pyrazolones can be classified into two types, that is, a process which comprises introducing a substituent into the 4-position of the pyrazolone ring after formation of the pyrazolone skeleton and a process which comprises previously introducing a substituent into a position corresponding to the 4-position of the pyrazolone ring and then forming the pyrazolone skeleton. Comparatively few examples of the latter process, which is described in British Pat. No. 1,284,649 and Japanese Patent Publication (OPI) No. 100057/75, are known. On the contrary, many examples concerning the former process wherein a substituent is introduced into the 4-position of the pyrazolone ring after formation of the 5-pyrazolone skeleton, which are described in, for example, U.S. Pat. Nos. 2,434,272, 3,148,062, 3,006,759, 3,522,051, 3,227,554, 3,701,783, 3,617,291, 3,311,476 and 3,419,391 and Japanese Patent Publication (OPI) No. 53372/75, are known.

Almost all of the above-described processes in which a substituent is introduced into the 4-position after formation of the pyrazolonering are not suitable, because there are restrictions on the preparation or on the structure of the compound. Namely, the desired compounds are obtained in a low yield because of long complicated steps and of the use of 4-amino-5-pyrazolones or 4-hydroxy-5-pyrazolones as starting materials or the desired compounds are prepared using complicated processings carried out after azo-coupling with 5-pyrazolones. Further, a linking group is limited to a sulfur or selenium containing group through an arylthio, alkylthio or heterocyclic thio group can be introduced directly to the 4-position of 5-pyrazolones by means of sulfenyl chloride.

SUMMARY OF THE INVENTION

An object of the present invention is to provide a process for introducing a nitrogen containing heterocyclic group into the 4-position of a 5-pyrazolone having an alkylamino, arylamino or N-heterocyclic amino group to produce 4-substituted compounds having a high purity in a high yield and a low cost.

A second object of this invention is to provide 5-pyrazolones having a high purity.

A third object of this invention is to provide 5-pyrazolone type couplers having excellent properties of color hue, resistance to color fading and color forming, a fourth object of this invention is to provide a novel process for producing 5-pyrazolones having a substituent at the 4-position which is releasable at oxidative coupling with p-phenylenediamine type color developing agents.

A fifth object of this invention is to provide a practical process for producing 4-substituted 5-pyrazolones.

The process of the present invention comprises replacing a hydrogen atom of the NH group in a 3-alkylamino-5-pyrazolone, a 3-arylamino-5-pyrazolones or a 3-N-heterocyclic amino-5-pyrazolone with a protective group, halogenating the resulting compound to introduce a halogen atom into the 4-position, replacing directly the halogen atom in the 4-position with a desired nitrogen containing heterocyclic group and hydrolyzing the resulting reaction product to remove the protective group, by which 3-N-substituted amino-4-substituted-5-pyrazolone compound having a nitrogen containing heterocyclic group in the 4-position are prepared.

DETAILED DESCRIPTION OF THE INVENTION

According to the process of the invention, it is possible to obtain in high purity and low cost 3-N-substituted amino-4-substituted-5-pyrazolones having a good color forming property and good color hue which are useful as DIR couplers or 2-equivalent couplers, because they can be prepared by a simple process in high yields from 3-N-substituted amino-5-pyrazolones as starting materials which are easily prepared.

A known process for preparing 4-monohalo-5-pyrazolones from 5-pyrazolone is described in U.S. Pat. No. 3,006,759. However, the halogenation in this process is highly affected by the substituent at the 3-position of the 5-pyrazolone. For example, where the substituent at the 3-position is an acid group, the product is substantially all 4-monohalo-5-pyrazolone. However, where the substituent at the 3-position is an anilino group, the product is a mixture of 4-monohalo-5-pyrazolone and 4-dihalo-5-pyrazolone in a molar ratio of nearly 1:1.

The replacement reaction of a 4-dihalo-5-pyrazolone does not proceed sufficiently and impurities are formed. Effective separation to obtain only the mono-substituted product is quite expensive because column chromatography is necessary for separation. Accordingly, a process for preparing intermediates necessary for synthesizing compounds in which one nitrogen-containing heterocyclic group is introduced into the 4-position of 3-alkylamino-5-pyrazolones, 3-arylamino-5-pyrazolones or 3-N-heterocyclic amino-5-pyrazolones in a high yield and a low cost by a simple process has been desired.

Very suitable results were obtained by substituting the hydrogen atom of the NH group in the 3-position with a suitable substituent (for example, an acyl group, an alkoxycarbonyl group or an aryloxycarbonyl group).

When the mono-halo compounds prepared by the above described process as preferred intermediates are used, it becomes possible to introduce a nitrogen containing heterocyclic group into the 4-position of 3-alkylamino-5-pyrazolones, 3-arylamino-5-pyrazolones or 3-N-heterocyclic amino-5-pyrazolones in a very high yield and a high purity by replacing directly the halogen atom at the 4-position of the mono-halo compounds with a nitrogen containing heterocyclic compound and hydrolyzing the resulting product. A reaction analogous to the above described substitution reaction is described in Japenses Patent Publication (OPI) No. 53372/75, where the halogen atom at the 4-position is replaced by a pyridine derivative, namely, a heteroaromatic compound having one nitrogen atom. However, this reaction is essentially different from that involved in the present invention, because the product is a 4-pyridino-5-pyrazolonyl-ylide, a so-called inner salt.

Further, the nitrogen containing heterocyclic compounds used in the present invention are structurally different from pyridines, because the former have a hydrogen atom which is dissociable while the latter does not have such a hydrogen atom. The nitrogen containing heterocyclic compounds used in the present invention from nitrogen containing heterocyclic metal salts by ion-exchange between a hydrogen atom and an alkali metal ion or an alkaline earth metal ion with ease, because they have a hydrogen atom which is dissociable. Since a halogen replacement reaction of a halogen compound represented by the general formula (III) is well known, a method in which halogen compounds and metal salts of a compound for replacement is used. However, the reaction of these nitrogen containing heterocyclic metal salts with halogen compounds represented by the formula (III) hardly proceeds unlike the conventional methods as stated above.

It is surprising that the replacement reaction proceeds under neutral conditions in the absence of a catalyst even though the nitrogen containing heterocyclic compounds used in the present invention are acid compounds since they have a dissociable hydrogen atom.

From this point of view, the present invention is also different from the reaction of basic materials which do not have a dissociable hydrogen atom such as the pyridines as described in Japanese Patent Publication (OPI) No. 53372/75.

The process for introducing directly a nitrogen containing heterocyclic group into the 4-position of 5-pyrazolones, which was a novel technique, could not previously be sufficiently utilized where compounds having an alkylamino, arylamino or N-heterocyclic amino group were used as starting materials. However, it has now become possible to sufficiently utilize the process by using the above described intermediates.

In the first step of the process of the present invention, a protective group is introduced into a 3-N-substituted-amino-5-pyrazolone as described in the following Reaction Schematic A:

Reaction Schematic A

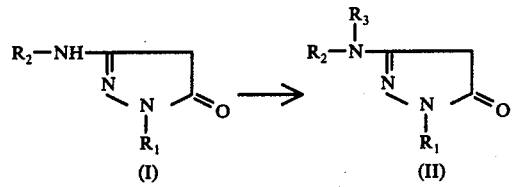

In the formulae (I) and (II), $R_1$ represents a hydrogen atom or has up to 35 carbon atoms, preferably up to 22 carbon atoms and represents a straight or branched alkyl group (for example, a methyl, isopropyl, tert-butyl, hexyl or dodecyl group, etc.), an alkenyl group (for example, an allyl group, etc), a cyclic alkyl group (for example, a cyclopentyl, cyclohexyl or norbornyl group, etc.), an aralkyl group (for example, a benzyl or β-phenylethyl group, etc), or a cyclic alkenyl group (for example, a cyclopentenyl or cyclohexenyl group, etc.), wherein the above described groups may be substituted with one or more substituents selected from halogen atoms (for example, fluorine, chlorine, etc.) and nitro, cyano, aryl (for example, phenyl, naphthyl, etc.), alkoxy (for example, methoxy, benzyloxy, etc.), aryloxy (for example, phenoxy, etc.) carboxy, alkylcarbonyl (for example, acetyl, etc.), arylcarbonyl (for example, benzoyl, etc.), alkoxycarbonyl (for example, methoxycarbonyl, benzyloxycarbonyl, etc.), aryloxycarbonyl (for example, phenoxycarbonyl, etc.), sulfo, acyloxy (for example, acetoxy, benzoyloxy, etc.), sulfamoyl (for example, N-methylsulfamoyl, N,N-dimethylsulfamcyl, etc.), carbamoyl (for example, carbamoyl, N-methylcarbamoyl, etc.), acylamino (for example, acetylamino, benzoylamino, etc.), diacylamino (for example, phthalimido, succinimido, etc.), ureido (for example, methylureido, phenylureido, etc.), thioureido (for example, methylthioureido, etc.), urethane (for example, methoxycarbonylamino, etc.), thiourethane (for example, phenoxythiocarbonylamino, etc.), sulfonamido (for example, methanesulfonamido, benzenesulfonamido, etc.), heterocyclic (for example, 2-pyridyl, 2-furyl, etc.), arylsulfonyloxy (for example, phenylsulfonyloxy, etc.), alkylsulfonyloxy (for example, ethylsulfonyloxy, etc.), arylsulfonyl (for example benzenesulfonyl, etc.), alkylsulfonyl (for example, methylsulfonyl, octadecylsulfonyl, etc.), arylthio (for example, phenylthio, p-nitrophenylthio, etc.), alkylthio (for example, phenylthio, p-nitrohenylthio, etc.), alkylthio (for example, ethylthio, tetradecylthio, etc.), alkylsulfinyl (for example, methylsulfinyl, dodecylsulfinyl, etc.), arylsulfinyl (for example, phenylsulfinyl, etc.), alkylamino (for example, propylamino, etc.) cycloalkylamino (for example, cyclohexylamino, etc.), dialkylamino (for example, N,N-diethylamino, etc.), anilino (for example, anilino, p-methoxyanilino, etc.), N-arylanilino (for example, N,N-diphenylamino, etc.), N-alkylanilino (for example, N-methyl-N-phenyl-amino, etc.), N-acylanilino (for example, N-acetylanilino, etc.), hydroxy and mercapto groups.

Further, $R_1$ has up to 35, preferably up to 22, carbon atoms and represents an aryl group (for example, a phenyl, α-naphthyl or β-naphthyl group, etc.) or an aryl group having one or more substituents. Suitable substituents include halogen atoms (for example, fluorine, chlorine, etc.), and alkyl (for example, methyl, dodecyl, etc.), alkenyl (for example, allyl, etc.), cycloalkyl (for example, cyclohexyl, etc.), aralkyl (for example, benzyl β-phenylethyl, etc.), cycloalkenyl (for example, cyclo-2-hexenyl, etc. Further, suitable substituents includ nitro, cyano, aryl, alkoxy, aryloxy, carboxy, alkylcarbonyl, arylcarbonyl, alkoxycarbonyl, aryloxycarbonyl, sulfo, acyloxy, sulfamoyl, carbamoyl, acylamino, diacylamino, ureido, thioureido, urethane, thiourethane, sulfonamido, heterocyclic, arylsulfonyloxy, alkylsulfonyloxy, arylsulfonyl, alkylsulfonyl, arylthio, alkylthio, alkylsulfinyl, arylsulfinyl, alkylamino, dialkylamino, anilino, N-alkylanilino, N-arylanilino, N-acylanilino, hydroxy and mercapto groups, of which specific examples of these groups have been given above.

Furthermore, $R_1$ has up to 35, preferably up to 22, carbon atoms and represents a heterocyclic group (for example, a 5- or 6-membered heterocyclic or condensed heterocyclic group having one or more of a nitrogen atom, an oxygen atom or a sulfur atom as heteroatoms, such as a pyridyl, quinolyl, furyl, benzothiazolyl, oxazolyl, imidazolyl or naphthoxazolyl group, etc.) or a substituted heterocyclic group having one or more of the substituents described above for the aryl group for $R_1$.

Moreover, $R_1$ represents an alkylcarbonyl group (for example, an acetyl, dodecanoyl group, etc.), an arylcarbonyl group (for example, a benzoyl, 2,4,6-trichlorobenzoyl group, etc.), an alkyl(thiocarbonyl) group (for example, a methyl(thiocarbonyl) group, etc.), an aryl(thiocarbonyl) group (for example, a phenyl(thiocarbonyl) group, etc.), an alkylsulfonyl group (for example, a methylsulfonyl, tetradecylsulfonyl group, etc.), an arylsulfonyl group (for example, a benzenesulfonyl, o-methylbenzenesulfonyl group, etc.), an alkylsulfinyl group (for example, a methylsulfinyl, octadecylsulfinyl group, etc.), an arylsulfinyl group (for example, a benzenesulfinyl group, etc.), a carbamoyl group (for example, a methylcarbamoyl, phenylcarbamoyl group, etc.) or a thiocarbamoyl group (for example, an ethylthiocarbamoyl, phenylthiocarbamoyl group, etc.).

In the formula (I) and (II), $R_2$ represents a hydrogen atom, or has up to 35, preferably up to 22, carbon atoms and represents an aryl group (for example, a phenyl, 4-methylphenyl, 2-chloro-5-nitrophenyl, 2-nitrophenyl, 2-chloro-5-tetradecyloxycarbonylaminophenyl, 2-chloro-5-sulfamoylphenyl, 2-chloro-5-carbamoylphenyl or 2-chloro-5-tetradecanamidophenyl group, etc.), a substituted aryl group having one or more of the substituents described above for the aryl group for $R_1$, an alkyl group (for example, an n-butyl, t-butyl, n-octadecyl,n-tetradecyl, benzyl or cyclohexyl group, etc.), a substituted alkyl group having one or more of the substituents described above for the alkyl group for $R_1$, a heterocyclic group (for example, a 2-pyridyl, 4-nitro-2-pyridyl, 4-tetradecanamido-6-pyrimidyl or 1-N-dodecyl-5-tetrazolyl group, etc.), or a substituted heterocyclic group having one or more of the substituents for the heterocyclic group for $R_1$.

In the formulae (I) and (II), $R_3$ has up to 35, preferably up to 22, carbon atoms and represents a formyl group, an alkylcarbonyl group (for example, acetyl, trichloroacetyl, etc.), an arylcarbonyl group (for example, phenylcarbonyl, etc.), an alkylsulfonyl group (for example, methanesulfonyl, etc.), an arylsulfonyl group (for example, benzenesulfonyl, etc.), an alkoxycarbonyl group (for example, a methoxycarbonyl or ethoxycarbonyl group, etc.), an aryloxycarbonyl group (for example, a phenoxycarbonyl group, etc.), a carbamoyl group (for example, a phenylcarbamoyl group, etc.), a thiocarbamoyl group (for example, a phenylthiocarbamoyl group, etc.) or a sulfamoyl group (for example, a phenylsulfamoyl group, etc.). Particularly preferred groups are alkylcarbonyl groups, alkoxycarbonyl groups and aryloxycarbonyl groups.

3-N-substituted amino-5-pyrazolones which can be used as starting materials in the process of the invention can be synthesized by the methods described in U.S. Pat. No. 3,515,429, U.S. Pat. No. 3,615,506, British Pat. No. 1,129,333 and British Pat. No. 1,129,334.

Preferred examples of 3-N-substituted amino-5-pyrazolones of the formula (I) which can be used as starting materials in the process of the present invention are as follows.

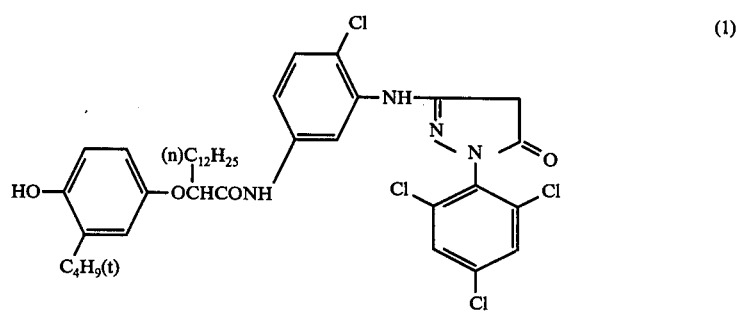

(1)

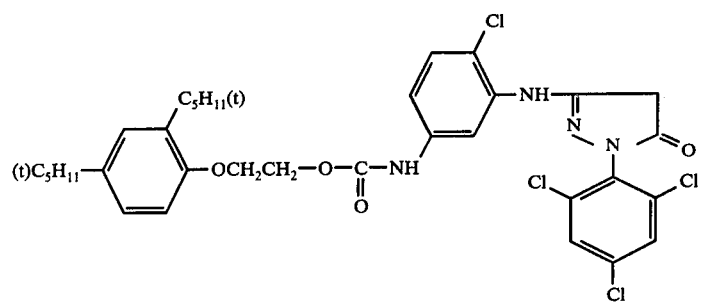
(2)
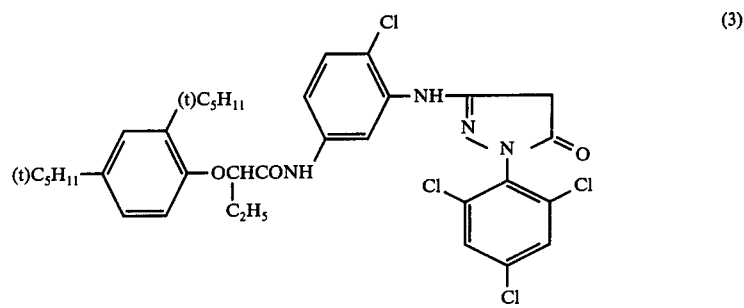
(3)
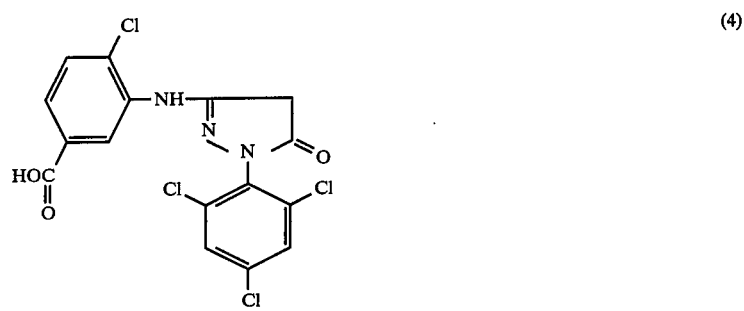
(4)
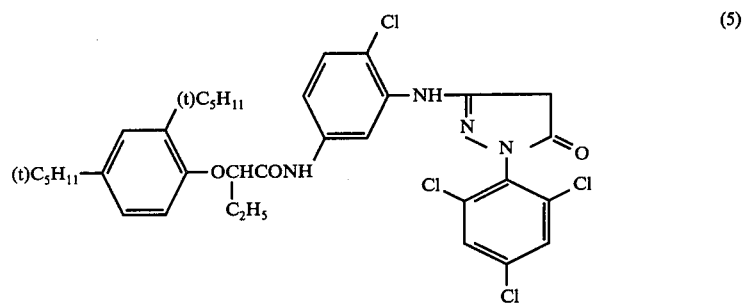
(5)
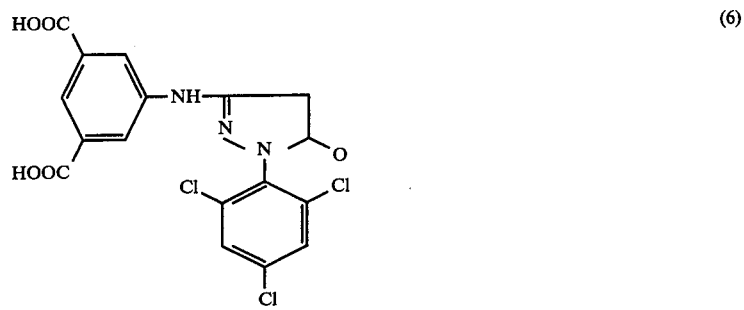
(6)

-continued
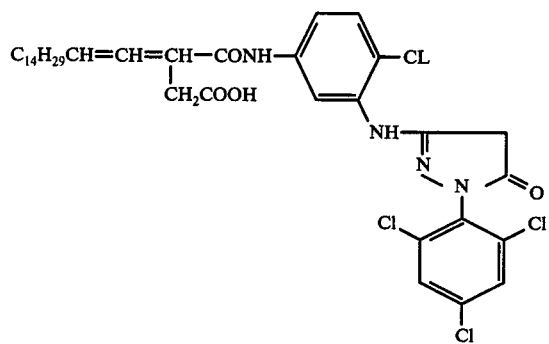 (7)
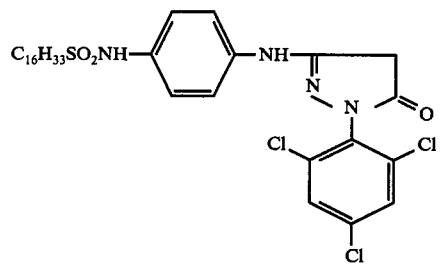 (8)
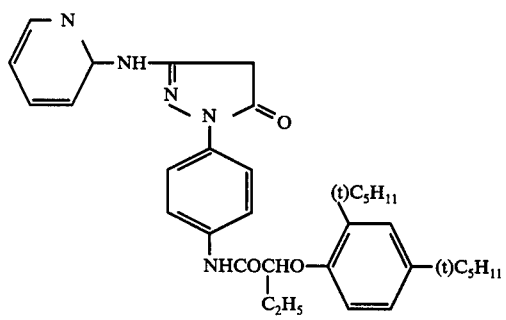 (9)
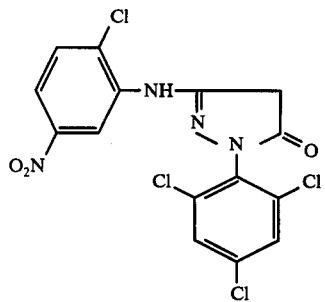 (10)
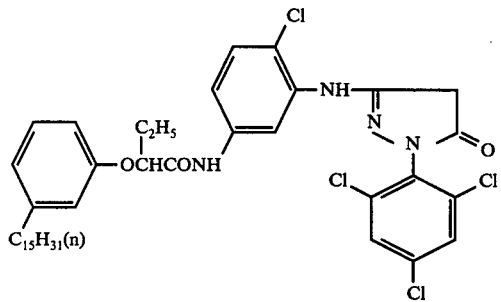 (11)

-continued
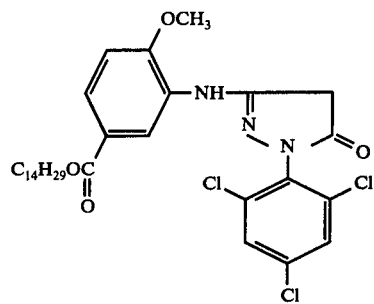
(12)
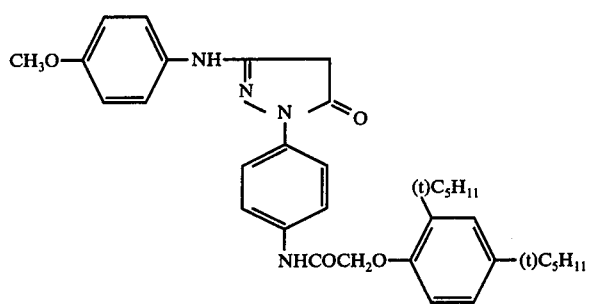
(13)
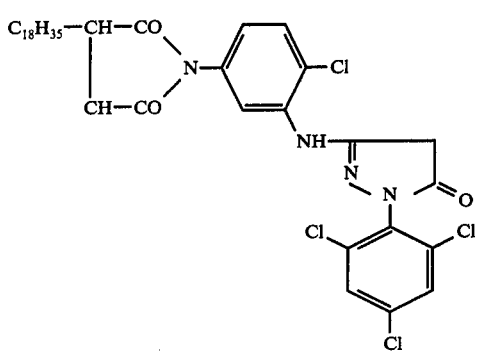
(14)
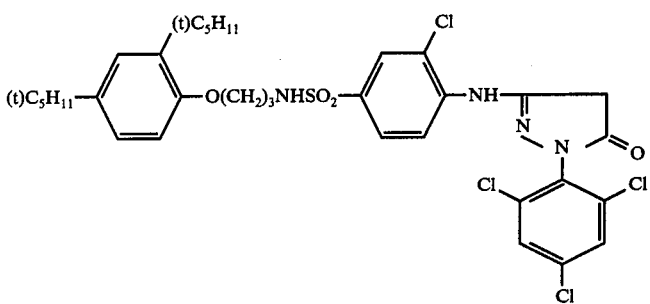
(15)
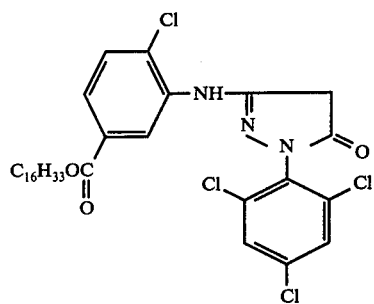
(16)

-continued
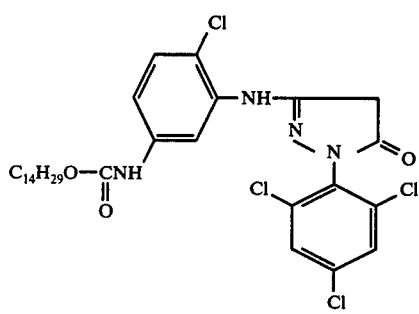 (17)
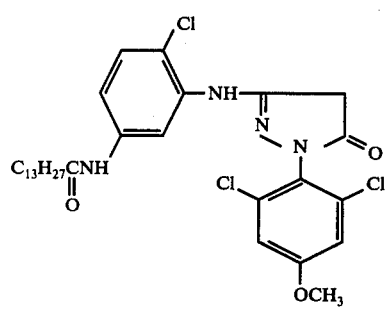 (18)
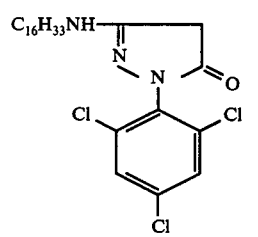 (19)
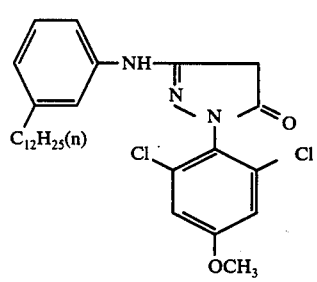 (20)
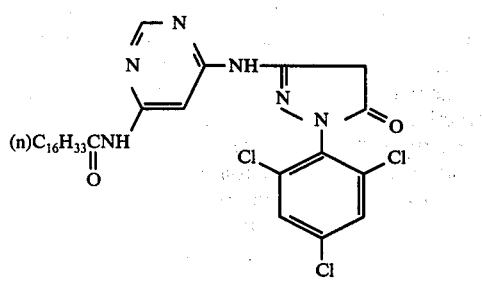 (21)

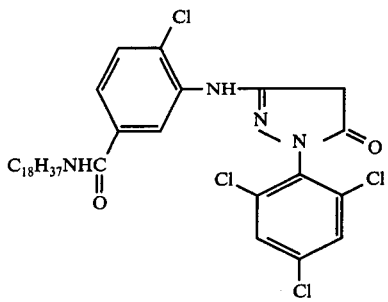

(22)

-continued

3-N-substituted anilino-5-pyrozolones are already described in Japanese Patent Publication (OPI) 71333/75. However, the N-substituent of the 3-N-substituted anilino-5-pyrazolones used in the present invention is utilized as a protective group, which is removed thereafter by hydrolysis. General processes for producing 3-N-substituted anilino-5-pyrazolones are described in the following.

It is possible to sythesize the corresponding 3-N-substituted anilino-5-pyrazolones by carrying out acylation, alkoxycarbonylation, sulfonylation, carbamoylation or thiocarbamoylation of 3-anilino-5-pyrazolone. Since acyl groups and alkoxycarbonyl groups are preferred as the protective groups, examples involving suchgroups are described in detail in the following.

In carrying out acylation or alkoxycarbonylation of 3-N-substituted anilino-5-pyrazolones, 3-N-substituted alkylamino-5-pyrazolones and 3-N-substituted heterocyclic amino-5-pyrazolones, an acylating agent (for example, an acyl halide, e.g., acetyl chloride or an acid anhydride, e.g., acetic anhydride, etc.) or an alkosycarbonlyatig agent (for example, an alkoxycarbonyl chloride, e.g., ethyl chloroformate, an alkoxycarbonyl chloride etc.) is added in an amount of about 1 to about 20 molar equivalents and the reaction is carried out at a temperature of about 0 to about 150° C. Although the reaction solvent used is not limited other than solvents which can be acylated such as alcohols are excluded, the reaction can be carried out using acetonitrile, aromatic hydrocarbons (for example, benzene or toluene, etc.), halogenated hydrocarbons (for example, chloroform, carbon tetrachloride, etc., ethers (for example, diethyl ether or dimethoxyethane, etc.), or carboxylic acids (for example, acetic acid or propionic acid, etcc.). In using an acylating agent or an alkoxycarbonylating agent which is liquid at room temperature (e.g., about 20°-30° C) or has a melting point of below about 100° C, the reaction can be carried out directly in the absence of a solvent without using a reaction solvent. After completion of the reaction, the solvent and the excess acylating agent or alkoxycarbonylating agent are removed or hydrolysis of the excess agent in a suitable manner is carried out to isolate the desired 3-N-substituted anilino-5-pyrazolones of the formula (II). In some cases of using certain kinds of acylating agents or alkoxycarbonylating agents, the 5-hydroxy group of the 3-N-substituted anilino-5-hydroxypyrazole is acylated or alkoycarbonylated by the acylating agent or the alkoxycarbonylating agent to form by-products. However, they can be selectively converted into 3-N-substituted anilino-5-pyrazolones using alkalis (for example, an aqueous solution of ammonia (about 1 to 10% by weight) or an aqueous solution of sodium hydroxide (about 1 to 10% by weight).

The reaction easily proceeds within about 30 minutes to about 24 hours.

In the second step of the process of the present invention, the compounds represented by the formula (II) prepared according to Reaction Schematic A are halogenated in accordance with the following Reaction Schematicc B.

Reaction Schematic B

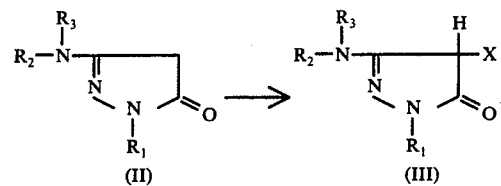

In the formulae (II) and (III), $R_1$, $R_2$ and $R_3$ each have the same meaning as described above, and X represents a chlorine atom, a broine atom or an iodine atom.

The compounds reepresented by the formula (III) can be prepared as follows.

A halogenating agent (chlorine, bromine, iodine or N-bromosuccinimide, N-chlorosuccinimide, sulfuryl chloride, phosphonyl chloride, phosphorous pentachloride, phosphorous tribromide, etc.) is added in a molar amount of about 1.0 to about 1.3to the compound represented by the formula (II), and the reaction is carried out at a temperature of about 0° to about 100° C. Suitable reaction solvents are carboxylic acids (e.g., acetic acid or propionic acid, etc.), halogenated hydrocarbns (e.g., chloroform or carbon tetrachloride, etc.), ethers (e.g., diethyl ether, dioxane or tetrahydrofuran, etc.), aprotic polar solvents (e.g., dimethylformamide or dimethylsulfoxide, etc.), alcohols (e.g., ethanol or methanol, etc.), aromatic hydrocarbons (e.g., benzene or toluene, etc.) and acetonitrile, etc. The reaction is generally completed within about 10 minutes to about 24 hours. After completion of the reaction, the compounds represented by the formula (III) can be obtained by removing the solvent and crystallizing them from a suitable solvent such as acetonitrile, n-hexane, ligroin, etc. or they can be obtained by extracting with a solvent having a high extraction capacity such as ethyl acetate or chloroform, washing with water, removing the extraction solvent and crystallizing the compounds.

The compounds represented by the formula (III) are then converted into compounds represented by the formula (V) by a replacement reaction in accordance with Reaction Schematic C.

Reaction Schematic C

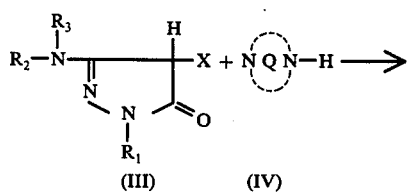

(III)    (IV)

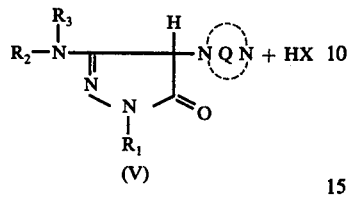

(V)

$R_1$, $R_2$, $R_3$ and X in formulae (III) and (V) above, each have the same meaning as described above.

Q represents a group of non-metallic atoms necessary to form a 5-membered or 6-membered heteroaromatic ring containing at least two nitrogen atoms as heteroatoms along with also additional nitrogen, oxygen and sulfur atoms as hetero atoms. Q may be unsubstituted or substituted with one or more substituents such as straight or branched alkyl, alkenyl, cycloalkyl, aralkyl and cycloalkkenyl groups each of which has up to 35 and preferably up to 22 carbon atoms (in which these groups may also be substituted with one or more substituents as described for $R_1$), aryl groups and heteerocyclic groups (in which the aryl and heterocyclic groups may be substituted with one or more substituents described for $R_1$), cyan, alkoxy (for example, methoxy, benzyloxy, etc.), aryloxy (for example, phenoxy, etc.), carboxy, alkoxycarbonyl (for example, methoxycarbonyl, benzyloxycarbonyl, etc.), aryloxycarbonyl (for example, phenoxycarbonyl, etc.), acyloxy (for example, acetoxy, benzoyloxy, etc.), alkylcarbonyl (for example, acetyl, etc.), arylcarbonyl (for example, benzoyl, etc.), alkylthiocarbonyl) (for example, methyl(thiocarbonyl), etc.), aryl(thiocarbonyl) (for example, phenyl(thiocarbonyl), etc.), sulfo, sulfamoyl (for example, N-methylsulfamoyl, N,N-dimethylsulfamoyl, etc.), carbamoyl (for example, carbamoyl, N-methylcarbamoyl, etc.), acylamino (for example, acetylamino, benzoylamino, etc.), diacylamino (for example, phthalimido, succinimido, etc.), ureido (for example, methylureido, phenylureido, etc.) thioureido (for example, methylthioureido, etc..), urethane (for example, methoxycarbonylamino, etc.), thiourethane (for example, phenoxythiocarbonylamino, etc.), sulfonamido (for example, methanesulfonamido, benzenesulfonamido, etc.), alkylsulfonyloxy (for example, ethylsulfonyloxy, etc.), arylsulfonyloxy (for example, phenylsulfonyloxy, etc.), arylsulfonyl (for example, benzenesulfonyl, etc), alkylsulfonyl (for example, methylsulfonyl, octadecylsulfonyl, etc.), arylthio (for example, phenylthio, P-nitrophenylthio, etc.), alkylthio (for example, ethylthio, teetradecylthio, etc.), alkylamino (for example, propylamino, etc.), cycloalkylamino (for example, cyclohexylamino, etc.), dialkylamino (for example, N,N-dimethylamino, etc.), anilino (for example, anilino, P-methoxyanilino, etc.), N-arylanilino (for examle, N,N-diphenylamino, etc.), N-alkylanilino (for example, N-methyl-N-phenylamino, etc.), N-acylanilino (for example, N-acetylanilino, etc.), hydroxy and mercato groups, and halogen atoms (for example, fluorine, chlorine, etc.), etc.

Further, Q represents not only a monocyclic ring but also a condensed ring containing a 5- or 6-membered ring. Examples of such ring systems condensed therewith include cyclohexene, cyclopentene, benzene, naphthalene and heteroaromatic rings (for example, pyridine, furan, oxazole, thiazole or thiophene rings etc.), which may be substituted with one or more of the substituents as described for Q.

Preferred N Q NH rings defined for Q are as follows, but Q is, not to be interpreted as being limited to these rings:

imidazole, 2-methylimidazole, 2-ethylimidazole, 2-chloroimidazole, 2-bromoimidazole, 2-($\beta$-hydroxyethyl)imidazole, 2,4-dimethylimidazole, 2-methyl-4-ethylimidazole, 2,4,5-trimethylimidazole, 4-methylimidazole, 4-chloroimidazole, 4-acetylimidazole, 4-methoxyimidazole, 2-($\beta$-phenoxyethyl)imidazole, 4-nitroimidazole, 4-cyanoimidazole, benzimidazole, 5-nitrobenzimidazole, 2-methylbenzimidazole, 5-bromobenzimidazole, 5-acetylaminobenzimidazole, 5-capronamidobenzimidazole, 1,2,3-triazole, 4,5-dimethyl-1,2,3-trizaole, 1,2,4-triazole, 3,5-diethyl-1,2,4-triazole, 3,5-dichloro-1,2,4-triazole, 3,5-di-($\beta$-methoxyethyl)-1,2,4-triazole, 3,5-dibenzyl-1,2,4-triazole, pyrazole, 3,5-dimethylpyrazole, 3-methyl-5-oxo-2-pyrazoline, 2-hydroxypyrimidine, 4-hydroxypyrimidine, 2-hydroxypyrazine, 2-hydroxypyridazine, indazole, 5-methylindazole, 5-acetylaminoindazole, 5-methoxyindazole, benzotriazole, 5-bromobenzotriazole, 5-nitrobenzotriazole, 5-methylbenzotriazole, 5-capronamidobenzotriazole, 5-benzyloxybenzotriazole, 5-octyloxybenzotriazole, 5-(3-methyl-2-benzothiazolinylidene)amino-benzotriazole, naphthotriazole, 1,2-dihydro-1-oxophthalazine, purine, xanthine, guanine, histidine, 4,5-dicarboxyimidazole, 4-carboxyimidazole, 5-hydroxy-1-phenyltetrazole and 5-methylthio-1-phenyltetrazole.

The compounds represented by the formula (V) above can be obtained by a process as described in the following.

In carrying out the reaction of a 4-halo-5-pyrazolone represented by the formula (III) with a nitrogen containing heterocyclic compound represented by the formula (IV), a temperature of about 10° to about 200° C is used and the reaction can be conducted without using a solvent or using an inert slvent such as benzene, acetone, toluene, acetonitrile, methanol, ethanol, diemthoxyethane, methyl Cellosolve, dimethylformamide, dimethylsulfoxide, N-methylpyrrolidone or hexamethylphosphotriamide, etc. The compound represented by the formula (III) is employed in an amount of about 1 to 20 times molar basis to the compound represented by the formula (IV) to produce the compound represented by the formula (V). However, the reaction temperature and the reaction time can be varied. The reaction can be preferably carried out at 50° to 150° C with 10 hours by adding the compound represented by the formula (IV) in an amount of about 2 to about 10 times on a molar basis to the compound represented by the formula (III). Where the compound represented by the formula (IV) has a melting point of below about 150° C, it is preferred to carry out the reaction with heating in the absence of a solvent. Further, where the compound represented by the formula (IV) has a melting point of above about 100° C, the reaction can be carried out using the above described organic solvent. In such cases, the organic solvent preferably is present in an amount of below about 20 times on a weight basis to the compound represented by the formula (IV). Further, the solvent is sufficiently used in such an amount that the compound represented by the formula (III) and the compound represented by the formula (IV) are dissolved by heating. The thus obtained substituted compound represented by the formula (V) is washed with water after adding a solvent having a high extraction capacity such as diethyl ether, ethyl acetate or chloroform etc. in an amount of about 2 to 10 times by volume of the reaction mixuter. The compound represented by the formula (IV) present in excess which is soluble in water can be removed by washing with water. The compound represented by the formula (IV) present in excess which is poorly soluble in water can be removed as the hydrochloride thereof by adding concentrated hydrochloric acid (about 30 to 40%) or by introducing gaseous hydrogen chloride into the system or can be removed by dissolving in water by adding an alkaline aqueous solution of sodium hydroxide or potassium hydroxide. Then, the extract solution is dried using a drying agent such as anhydrous sodium sulfate or anhydrous magnesium sulfate and concentrated, by which the compound represented by the formula (V) can be obtained in a high purity.

A feature of this step of the process is to add the compound represented by the formula (IV) in a neutral condition to react with the compound represented by the formula (III), and thus the compound represented by the formula (IV) functions as a hydrogen halide acceptor. This step proceeds very effectively and the desired compound represented by the formula (IV) having a high purity can be easily obtained after simple work-up procedures.

In order to obtain the desired compounds of the formula (IV), the compounds represented by the formula (V) are hydrolyzed according to the following Reaction Schematic D.

Reaction Schematic D

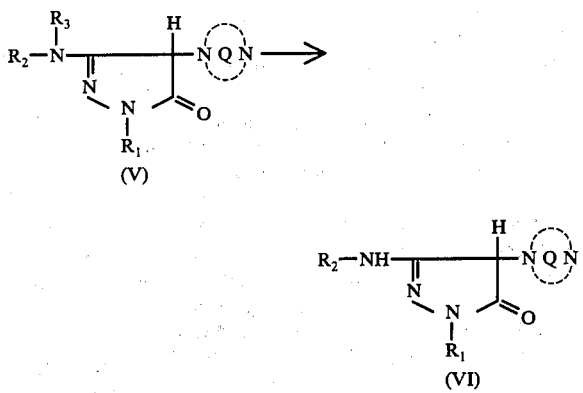

The above described hydrolysis reaction can be carried out as follows.

An alkali agent (for example, a solution of ammonia in methanol (about 5 to 20% by weight), a solution of sodium hydroxide or potassium hydroxide in methanol (about 5 to 20% by weight) or an aqueous solution of sodium hydroxide or potassium hydroxide (about 2 to 20% by weight) is employed in an amount of about 1 to about 100 times on a molar basis to the compound represented by the formula (V), and the reaction is carried out at about 0° to about 100° C,. Suitable reaction solvents which can be used are alcohols (e.g., methanol or ethanol, etc.), water, ethers (e.g., diethyl ether or dioxane, etc.), aprotic polar solvents (e.g., dimethylformamide, etc.) and aromatic hydrocarbons (e.g., benzene or toluene, etc.). The hydrolysis reaction is generally completed within about 30 minutes to about 24 hours. After completion of the reaction, the reaction mixture is neutralized with an acid (for example, acetic acid, an aqueous solution of hydrochloric acid (about 1 to 30% by weight) an aqueous solution of sulfuric acid (about 1 to 30% by weight), or gaseous hydrogen chloride, etc.) and extracted with a solvent having a high extraction capacity such as ethyl acetate, chloroform or diethyl ether, etc. The extract solution is washed with water and the solvent is removed to crystallize the desired compound. Where the desired compound is crystallized when neutralized with the acid, the crystals are separated by filtration and washed well with water. Thus, the compound represented by the formula (VI) having a high purity can be obtained.

In the present invention, Reaction Schematics A and B proceed very effectively to yield only the compound represented by the formula (III) which is a monohalogenated compound. Accordingly, it is not necessary to carry out costly procedures such as separation of the monohalogenated compound and the dihalogenated compound. Further, Reaction Schematic C proceeds very effectively to yield the compound represented by the formula (V) in a yield of nearly 100%, and therefore, a complicated purification process is not necessary.

Thus, according to the process of the present invention comprising the steps respresented by Reaction Schenatics A, B, C and D, the compounds represented by the formula (VI) having a high purity can be obtained in a low cost in simple steps from the compounds represented by the formula (I) as starting materials.

Thus, it becomes possible for the first time to produce the compounds represented by the formula (VI) which have excellent properties in hue and color forming ability as 2-equivalent couplers or as magenta DIR couplers in simple steps in a high purity and a low cost, if the steps represented by Reaction Schematics A, B, C and D are combined as described above.

Examples of compounds which can be prepared according to the present invention are described below.

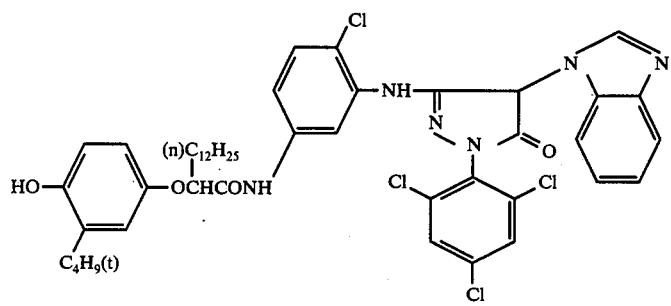
(1)
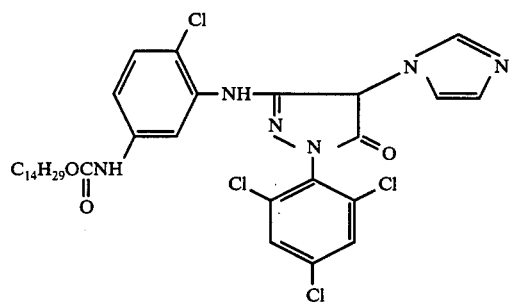
(2)
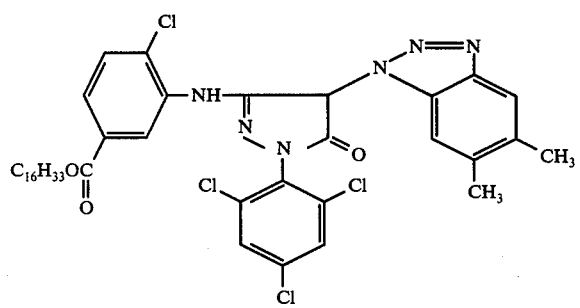
(3)
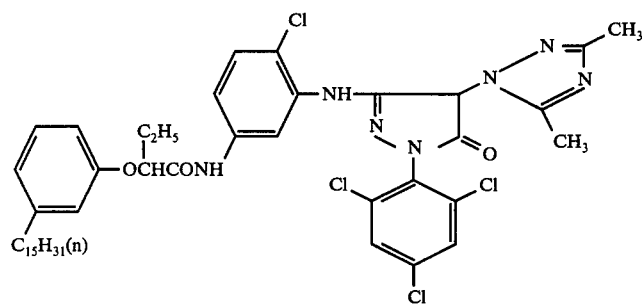
(4)
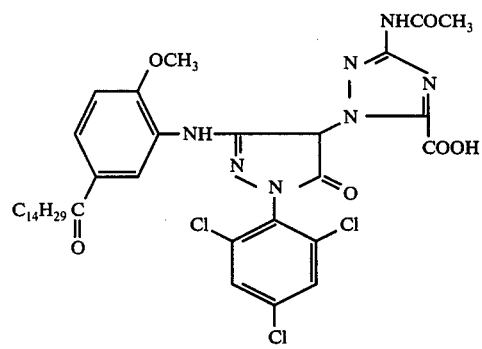
(5)

-continued
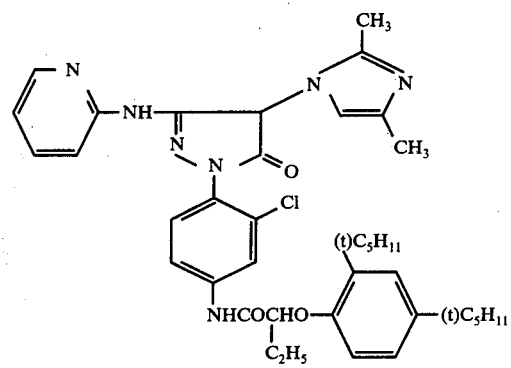 (6)
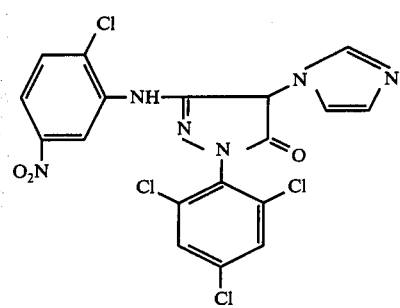 (7)
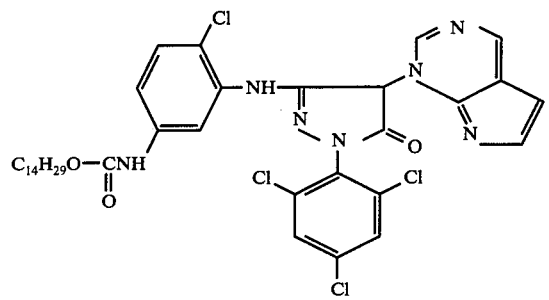 (8)
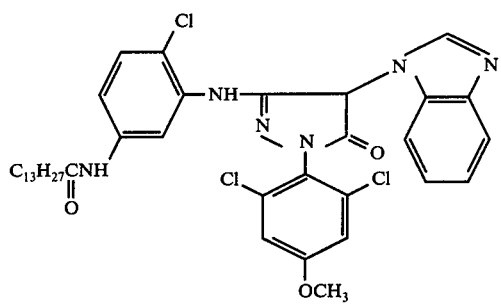 (9)
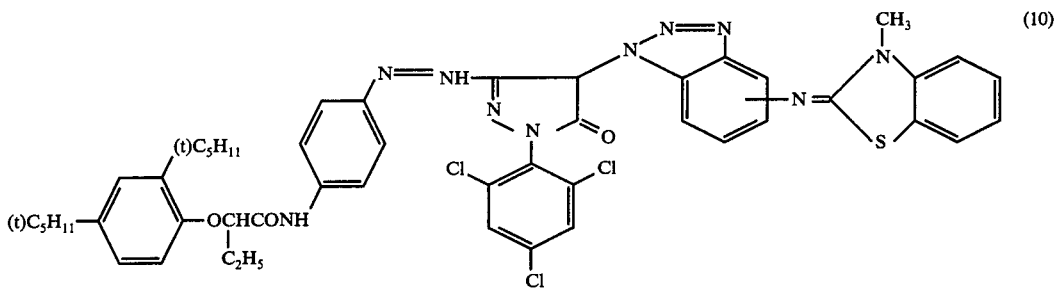 (10)

-continued
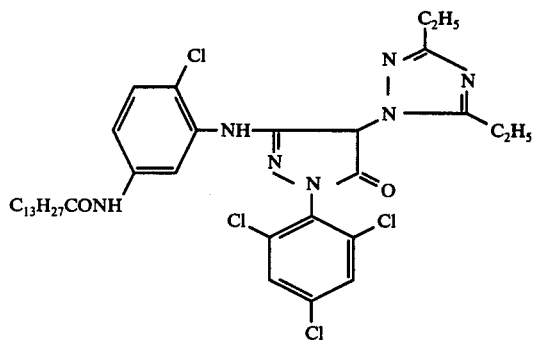 (11)
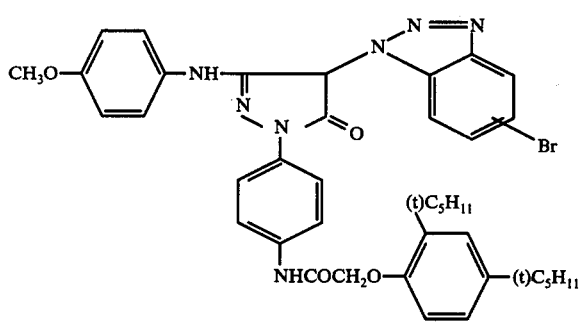 (12)
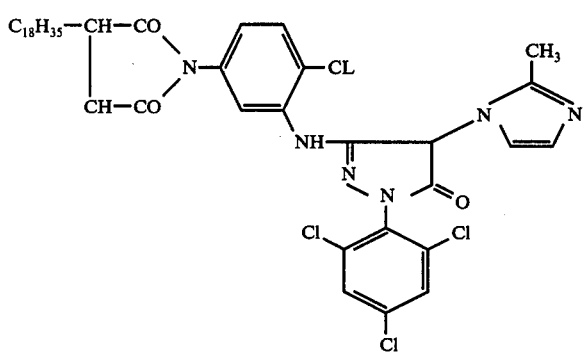 (13)
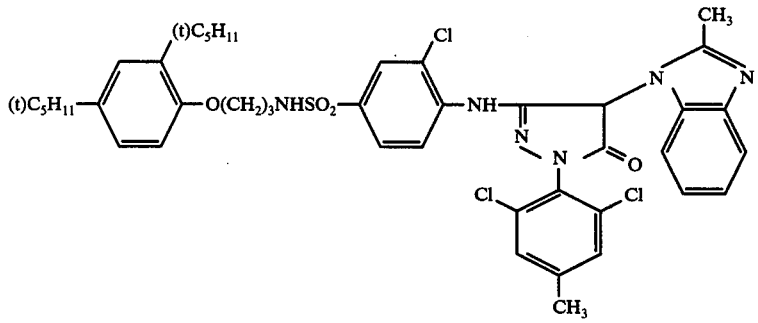 (14)
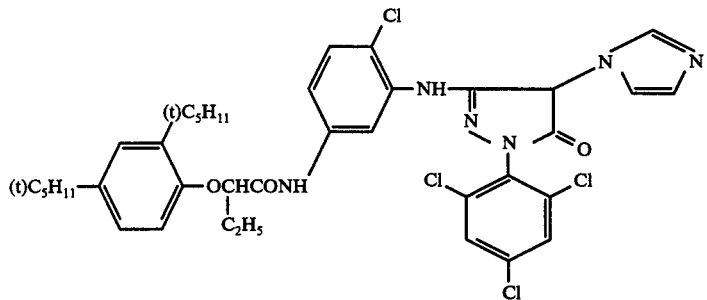 (15)

-continued
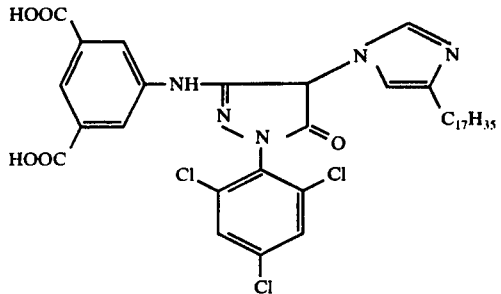 (16)
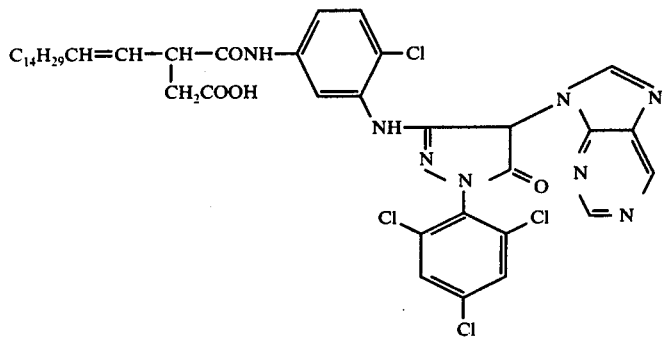 (17)
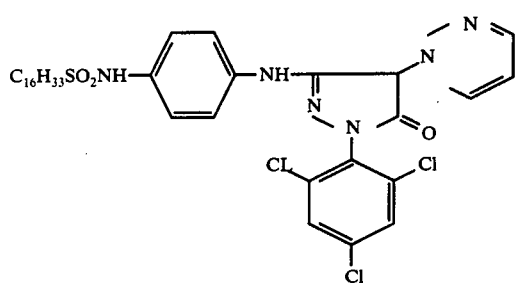 (18)
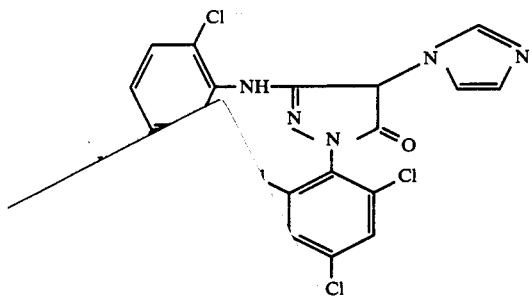 (19)
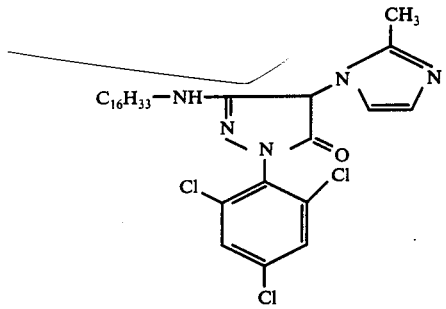 (20)

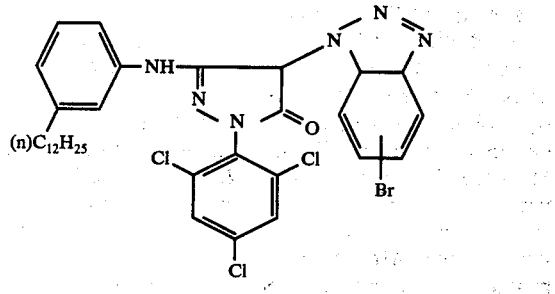

(21)

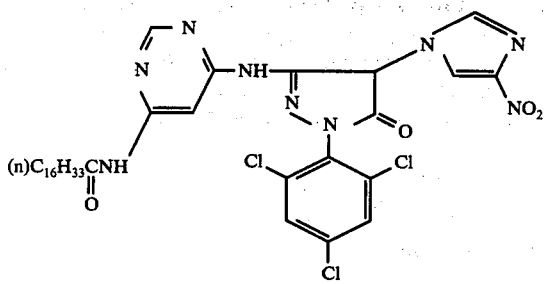

(22)

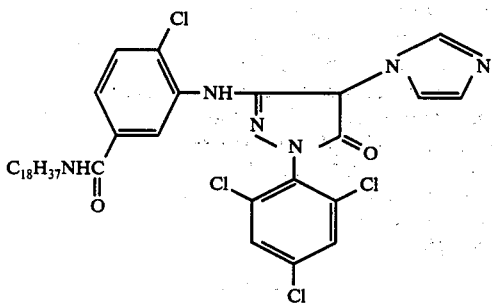

(23)

The following specific examples are given to illustrate the process of the present invention in greater detail. Unless otherwise indicated, all parts, percents, ratios and the like are by weight.

EXAMPLE 1

Synthesis of 1-(2,4,6-Trichlorophenyl)-3-(2-chloro-5-nitoanilino)4-(1-imidazolyl)-5-oxo-2-pyrazoline:

Intermediate (1); Synthesis of 1-(2,4,6-trichlorophenyl)-3-[N-acetyl-(2-chloro-5-nitro)anilino]-5-oxo-2-pyrazoline ammonium salt:

310 g of 1-(2,4,6-trichlorophenyl)-3-(2-chloro-5-nitrol)anilino-5-oxo-2-pyrazoline was dissolved in 400 ml of acetic acid anhydride and 15 g of zinc chloride was added thereto. The mixture was stirred for 4 hours at 70° to 80° C. After reaction, the mixture was colled with water over night and the precipitated solid was separated by filtration. This solid ws dispersed in 1.5 liters of ethyl acetate and 70 ml of an aqueous solution of ammonia (10%) was added thereto with stirring at room temperature. The system initially became homogeneous, but after a few minutes a light yellow solid precipitated. After separation by filtration, the solid was washed with water and dried, by which 273 g of the title compound was obtained. Melting point: 120° - 123° C.

Intermediate (2): Synthesis of 1-(2,4,6,-trichlorophenyl)-3-[N-acetyl-(2-chloro-5-nitro)anilino]-4-bromo-5-oxo-2-pyrazoline;

155 g of the above described Intermediate (1) was dissolved in 500 ml of acetic acid and 50.3 g of bromine was added dropwise over a 3 hour period at room temperature with stirring. After the addition, the stirring was continued for 1 hour and the precipitated solid was separated by filtration and washed with water. By recrystallization using 1 liter of acetonitrile, 132 g of the title compound was obtained.

Melting point: 133°-135° C.

Intermediate (3) Synthesis of 1-(2,4,6-trichlorophenyl)-3-[N-acetyl-(2-chloro-5-nitro)anilino]-4-(1-imidazolyl)-5-oxo-2-pyrazoline:

287 g of the above described Intermediate (2) was mixed with 142 g of imidazole and the mixture was heated for 5 hours in an oil bath at 130° C with stirring. After completion of the reaction, 700 ml of acetic acid was added to dissolve the reaction product. The resulting solution in acetic acid was poured into 2 liters of ice-water and a precipitated solid was separated by filtration. After the precipitation was washed with water, it was washed with 500 ml of hot methanol (40°-50° C), separated by filtration and dried to obtain 188 g of pure Compound. Melting point: Above 250° C.

Elemental Analysis: $C_{20}H_{12}N_6O_4Cl_4$ Calculated C(44.3%) H(2.21%) N(15.4%) Found: C(44.08%) H(2.49%) N(15.59%)

Synthesis of Coupler (7) Synthesis of 1-(2,4,6-trichlorophenyl)-3-(2-chloro-5-nitro-anilino)-4-(1-imidazolyl)-5-oxo-2-pyrazoline (Coupler (7)):

188 g of the above described Intermediate (3) was dissolved in 1 liter of a 5% KOH/methanol solution and the resulting solution was allowed to stand overnight. 500 ml of acetic acid was then added thereto and the solution was condensed to one third of its volume. The residual solution was poured into 2 liter of icewater, and a precipitated yellow solid was separated by filtration and washed with water. The resulting solid was dispersed in 1 liter of acetonitrile at room temperature. After stirring for 2 hours, the solid was separated by filtration and dried to obtain 27 g of Coupler (7).

Melting point: above 250° C

Elemental Analysis: $C_{18}H_{10}N_6O_3Cl_4$ Calculated: C(43.2%) H(2.02%) N(16.8%) Found: C(43.01%) H(2.05%) N(17.05%)

Synthesis of Coupler (10)

9.0 g of the above described Intermediate (4) was dissolved in 100 ml of acetic acid. To the solution, 9.0 g of granulated iron and 5 ml of water was added. After heating (80°-90° C) for 30 minutes on a water bath with stirring, the solution was cooled (10°-20° C) with water. 2.0 g of sodium acetate and 6.2 g of α-ethyl-(2,4,-di-tert-pentylphenoxy)acetyl chloride were added to the solution. After reacting for 30 minutes, the reaction solution was filtered. The filtrate was extracted with 300 ml of ethyl acetate and 500 ml of water. After washing the organic phase with water, it was dried with anhydrous sodium sulfate. Ethyl acetate was then removed by distillation and the residue was crystallized with 200 ml of a mixture of acetonitrile and ethyl acetate (1/1 by volume).

It was further recrystallized with 200 ml of a mixture of acetonitrile and ethanol (2/1 by volume), by which 9.2 g of Coupler (10) was obtained.

Melting point: 418°-151° C

Elemental Analysis: $C_{38}H_{42}N_6O_3Cl_4$ Calculated: C(59.4%) H(5.46%) N(10.9%) Found: C(59.19%) H(5.55%) N(11.12%).

Comparison Example 1

4.4 g of 1-(2,4,6-trichlorophenyl)-3-(2-chloro-5-nitroanilino)-5-oxo-2-pyrazoline was dissolved in 50 ml of dimethylformamide. To this solution, a solution of 2.4 g of bromine in 10 ml of dimethylformamide was added dropwise at 25° C. Addition of the bromine solution was carried out slowly with stirring while progress of the reaction was followed by thin layer chromatography. Thin layer chromatography showed that the product was composed of a mixture of nearly a molar ratio 1:1 of a compound wherein two bromine atoms were introduced into the starting material and a compound wherein one bromine atom was introduced into the starting material. When this product was reacted with imidazole in the same manner as described above for preparing Intermediate (3) instead of Intermediate (2) in the process, a mixture of 1-(2,4,6-trichlorophenyl)-3-(2-chloro-5-nitroanilino)-5-oxo-2-pyrazoline as the starting material, a compound wherein two bromine atoms were introduced into the 4-position of the starting material, a compound wherein two imidazole rings were introduced into the 4-position of the starting material, 1-(2,4,6-trichlorophenyl)-3-(2-chloro-5-nitroanilino)-4-(1-imidazolyl)-5-oxo-2-pyrazoline (Coupler 7) and several materials of unknown chemical structure were obtained. In order to obtain the desired compound from this mixture, only a method of column separation could be used.

EXAMPLE 2

Synthesis of 1-(2,4,6-Trichlorophenyl)-3-(2-chloro-5-tetradecanamido)anilino-4-(3,5-diethyl-1,2,4-triazolyl-1)-5-oxo-2-pyrazoline (Coupler (11):

Intermediate (1): Synthesis of 1-(2,4,6-trichlorophenyl)-3-(N-acetyl-(2-chloro-5-tetradecanamido)anilino)-4-(3,5-diethyl-1,2,4-triazolyl-1)-5-oxo-2-pyrazoline:

22.0 g of 1-(2,4,6-trichlorophenyl)-3-[N-acetyl-(2-chloro-5-tetradecanamido)anilino]-4-bromo-5-oxo-2-pyrazoline (prepared according to the process for preparing Intermediate (2) in Example 1. Melting point: 167°-169° C) was mixed with 12.0 g of 3,5-diethyl-1,2,4-triazole. After adding 10 ml of hexamethylphosphotriamide the mixture was heated in an oil bath at 100° C with stirring. After reacting for 12 hours, the reaction product was dissolved in 500 ml of ethyl acetate and washed 3 times with 500 ml of water. After the organic phase was dried with anhydrous sodium sulfate, it was condensed and the residue ws crystallized from 300 ml of a mixture of ethyl acetate and acetonitrile (one half by volum), by which 18 g of the desired compound was obtained.

Melting point: 240°-242° C.

Synthesis of Coupler (6):

18 g of the above described Intermediate (1) was dissolved in 200 ml of a 10% KOH/methanol solution, and the solution was stirred for 15 hours at room temperature. After adding 100 ml of acetic acid, the solution was condensed to one half its volume. The residual solution was poured into 500 ml of ice-water. The precipitated solid was separated by filtration, washed with water and recrystallized from 100 ml of acetonitrile, by which 12.6 g of Coupler (6) was obtained.

Melting point: 225°-226° C.

Elemental Analysis $C_{35}H_{45}N_7)_2Cl_4$ Calculated: C(57.0%) H(6.15%) N(13.3%) Found: C(56.86%) H(6.15%) (N13.17%)

Comparison Example 2

6.1 g of 1-(2,4,6-trichlorophenyl)-3-(2-chloro-5-tetradecanamido)anilino-5-oxo-2-pyrazoline was dissolved in 50 ml of dimethylformamide. To the resulting solution, a solution of 2.4 g of bromine in 10 ml of dimethylformamide was added dropwise at 25° C. The resulting product was a mixture of a compound wherein one bromine atom was introduced into the 4-position of the above described compound and a compound wherein two bromine atoms were introduced into the 4-position of the above described compound similar to the case of Comparison Example 1.

While the invention has been described in detail and with reference to specific embodiments thereof, it will be apparent to one skilled in the art that various changes and modifications can be made therein without departing from the spirit and scope thereof.

What is claimed is:

1. A process for preparing a 3-N-mono-substituted amino-4-substituted-5-pyrazolone represented by the formula (VI)

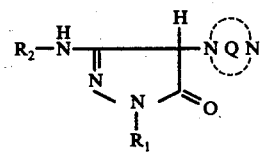

(VI)

wherein $R_1$ represents a hydrogen atom or has up to 35 carbon atoms and represents a straight or branched alkyl group, an alkenyl group, a cycloalkyl group, an aralkyl group, a cycloalkenyl group, an aryl group, a heterocyclic group, an acyl group, a thioacyl group, an alkylsulfonyl group, an arylsulfonyl group, an alkylsulfinyl group, an arylsulfinyl group, a carbamoyl group or a thiocarbamoyl group; $R_2$ represents a hydrogen atom or has up to 35 carbon atoms and represents an alkyl group, an aryl group or a heterocyclic group; and Q represents a group of nonmetallic atoms necessary to form a 5-membered or 6-membered heterocyclic ring containing two or more nitrogen atoms;

which comprises replacing the hydrogen atom of the N-H group in the 3-position of a compound represented by the formula (I)

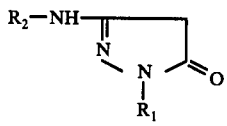
(I)

wherein $R_1$ and $R_2$ are as described above; with a protective group to prepare a compound represented by the formula (II)

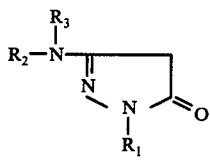
(II)

wherein $R_1$ and $R_2$ are as described above, and $R_3$ has up to 35 carbon atoms and represents a formyl group, an alkyl carbonyl group, an aryl carbonyl group, an alkyl sulfonyl group, an arylsulfonyl group, an alkoxycarbonyl group, an aryloxycarbonyl group, a carbamoyl group, a sulfamoyl group or a thiocarbamoyl group; halogenating the resulting compound represented by the formula (II) to prepare a compound represented by the formula (III)

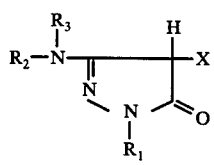
(III)

wherein $R_1$, $R_2$ and $R_3$ are as described above, and X represents a halogen atom;

reacting the resulting compound represented by the formula (III) with a nitrogen-containing heterocyclic compound represented by the formula (IV)

(IV)

wherein Q is as described above; to prepared a compound represented by the formula (V)

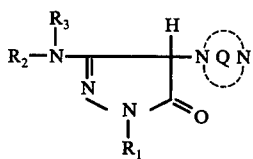
(V)

wherein $R_1$, $R_2$, $R_3$ and Q are as described above; and converting the resulting compound of the represented by the formula (V) into a compound represented by said formula (VI).

2. The process of claim 1, wherein the replacing of the hydrogen atom of the N-H group in the 3-position of the compound represented by the formula (I) is by acylating the compound represented by the formula (I) with an acylating agent or an alkoxycarbonylating agent in an amount of about 1 to about 20 molar equivalents to the compound represented by the formula (I) at a temperature of about 0° to about 150° C in the absence of a solvent or in the presence of an inert solvent; wherein the halogenating of the compound represented by the formula (II) is with a halogenating agent in a molar equivalent amount to the compound represented by the formula (II) at a temperature of about 0° to about 100° C in the presence of an inert solvent; wherein the reacting of the compound represented by the formula (III) is with said nitrogen-containing heterocyclic compound represented by the formula (IV) in a molar equivalent amount of about 1 to 20 times to the compound represented by the formula (III) at a temperature of about 10° to about 200° C in the absence of a solvent or in the presence of an inert solvent; and wherein the converting of the compound represented by the formula (V) to the compound represented by the formula (VI) is by hydrolysis in the presence of an alkali in an amount of about 1 to about 100 times on a molar basis to the compound represented by the formula (V) at a temperature of about 0° to about 100° C in the presence of an inert solvent.

3. The process of claim 1, wherein Q represents a group of non-metalic atoms necessary to form a 5- membered or 6- membered heterocyclic ring containing two or more nitrogen atoms selected from the group consisting of imidazole, 2-methylimidazole, 2-ethylimidazole, 2-chloroimidazole, 2-bromoimidazole, 2-($\beta$-hydroxyethyl)imidazole, 2,4-dimethylimidazole, 2-methyl-4-ethylimidazole, 2,4,5-trimethylimidazole, 4-methylimidazole, 4-chloroimidazole, 4-acetylimidazole, 4-methoxyimidazole, 2-($\beta$-phenoxyethyl)imidazole, 4-nitroimidazole, 4-cyanoimidazole, benzimidazole, 5-nitrobenzimidazole, 2-methylbenzimidazole, 5-bromobenzimidazole, 5-acetylaminobenzimidazole, 5-capronamidobenzimidazole, 1,2,3-triazole, 4,5-dimethyl-1,2,3-triazole, 1,2,4-triazole, 3,5-diethyl-1,2,4-triazole, 3,5-dichloro-1,2,4-triazole, 3,5-di-($\beta$-methoxyethyl)-1,2,4-triazole, 3,5-dibenzyl-1,2,4-triazole, pyrazole, 3,5-dimethylpyrazole, 3-methyl-5-oxo-2-pyrazoline, 2-hydroxypyrimidine, 4-hydroxypyrimidine, 2-hydroxypyrazine, 2-hydroxypyridazine, indazole, 5-methylindazole, 5-acetylaminoindazole, 5-methoxyindazole, benzotriazole, 5-bromobenzotriazole, 5-nitrobenzotriazole, 5-methylbenzotriazole, 5-capronamidobenzotriazole, 5-benzyloxybenzotriazole, 5-octyloxybenzotriazole, 5-(3-methyl-2-benzothiazolinylidene)amino-benzotriazole, naphthotriazole, 1,2-dihydro-1-oxophthalazine, purine, xanthine, guanine, histidine, 4,5-dicarboxyimidazole, 4-carboxyimidazole, 5-hydroxy-1-phenyltetrazole or 5-methylthio-1-phenyltetrazole.

4. The process of claim 1, wherein said temperature of about 10° to about 200° C is 50° to 150° C.

5. The process of claim 1, wherein said 3-N-monosubstituted amino-4-substituted-5-pyrazolone represented by the formula (VI) is selected from the group consisting of
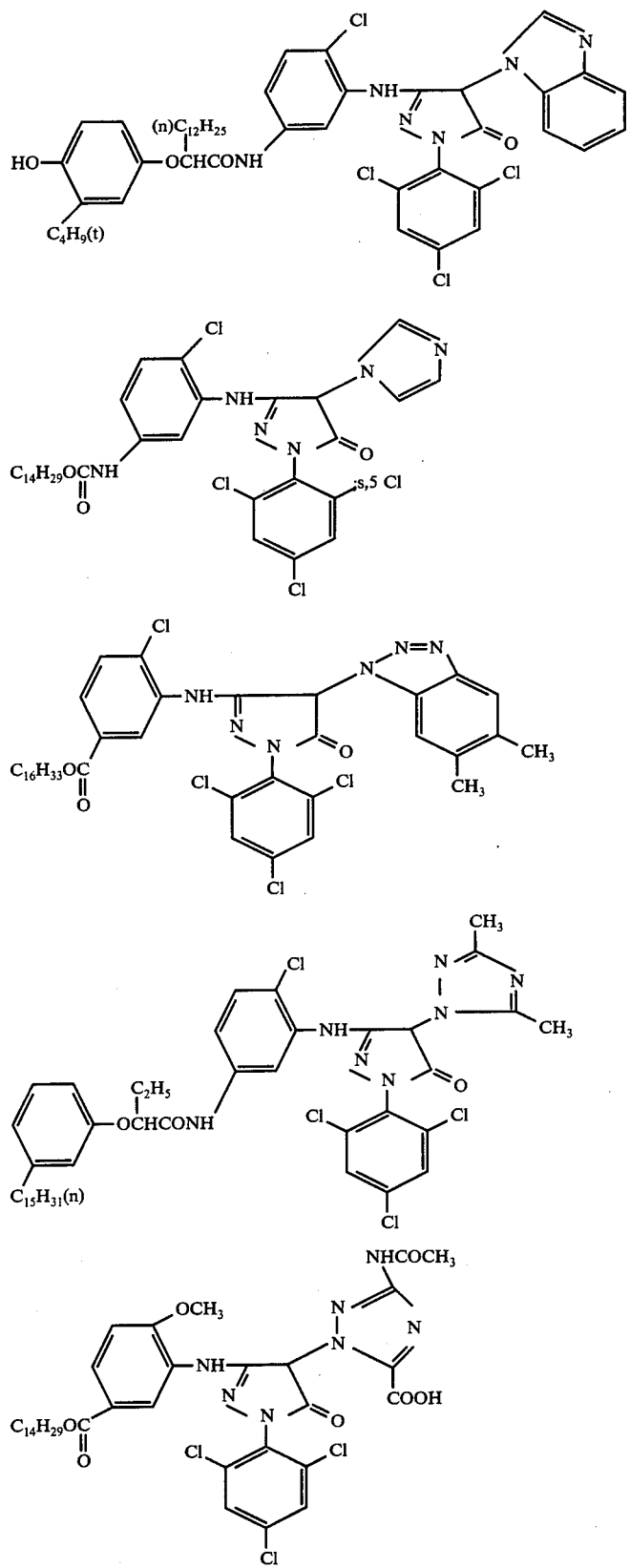

-continued
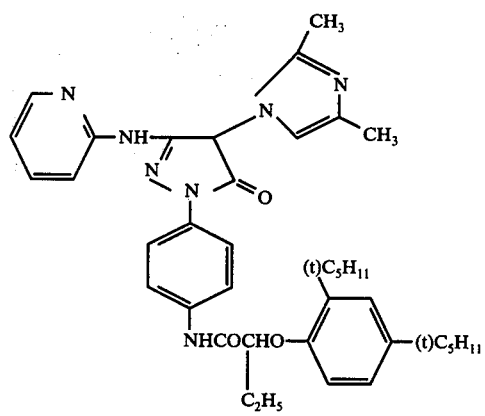
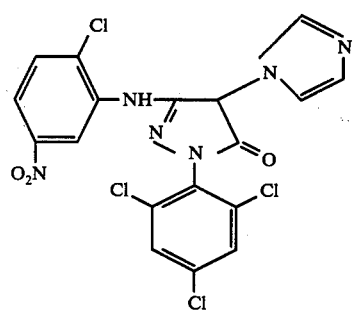
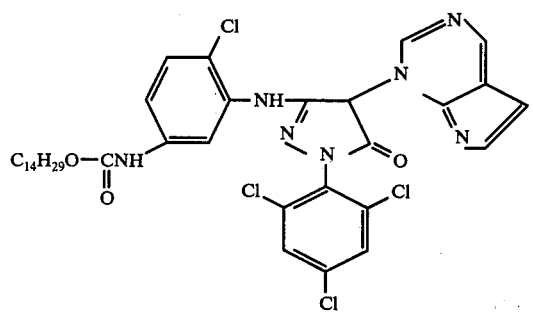
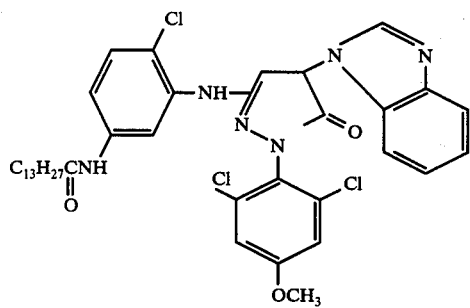
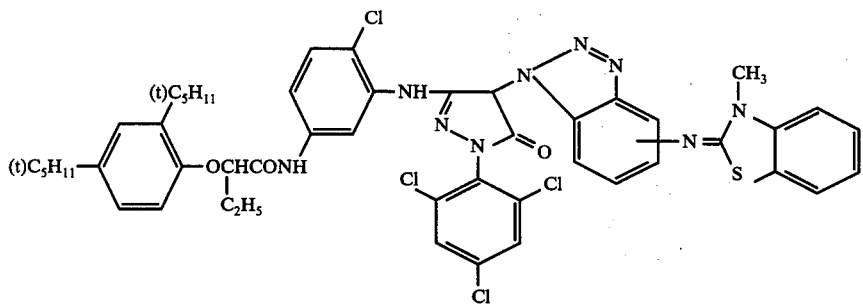

-continued
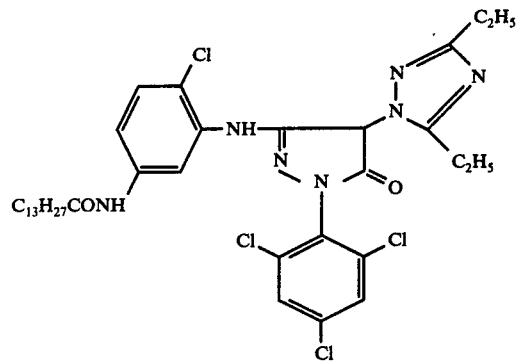
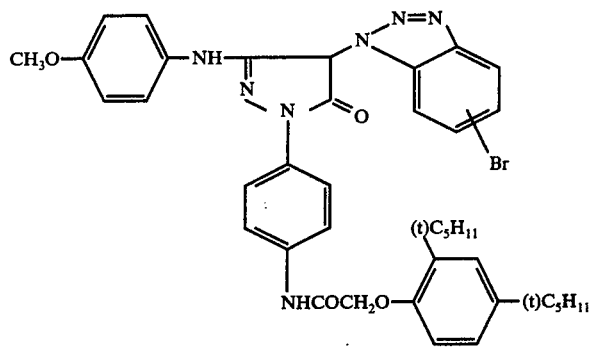
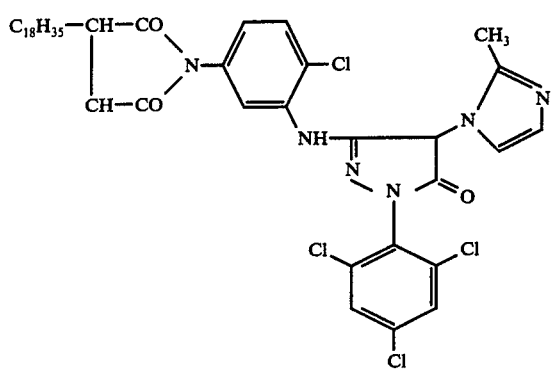
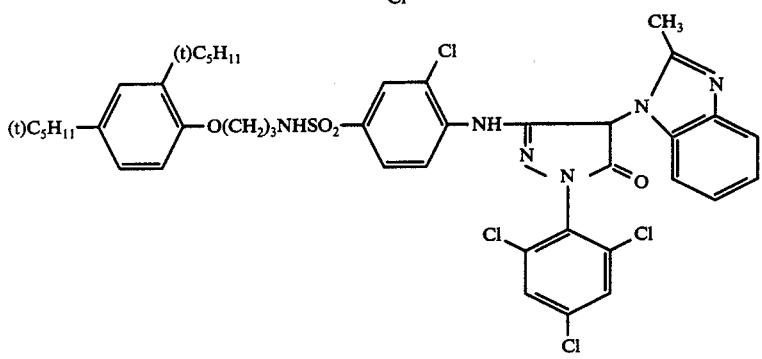
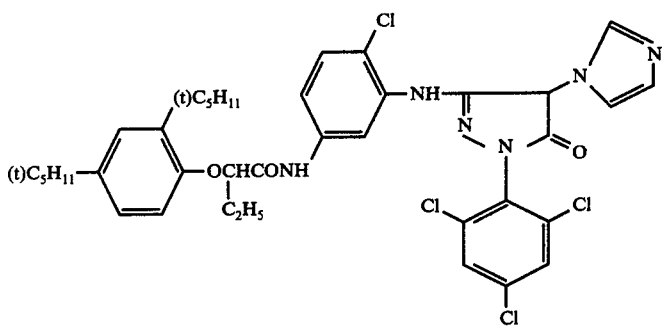

-continued
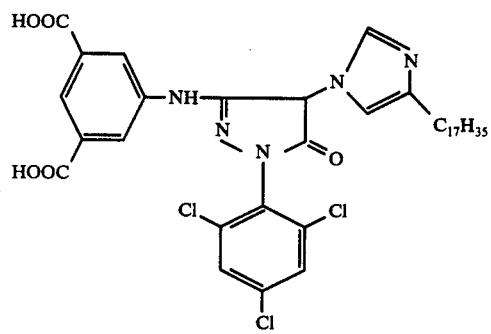
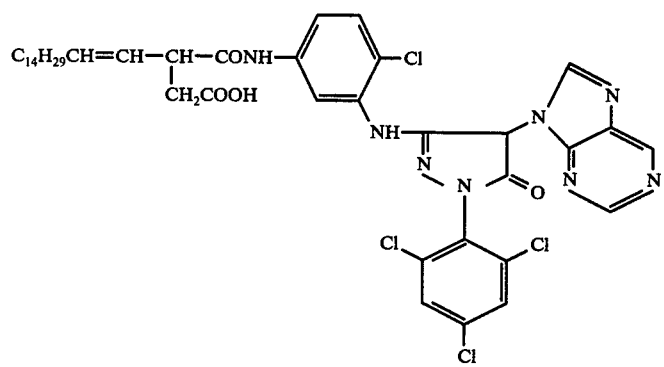
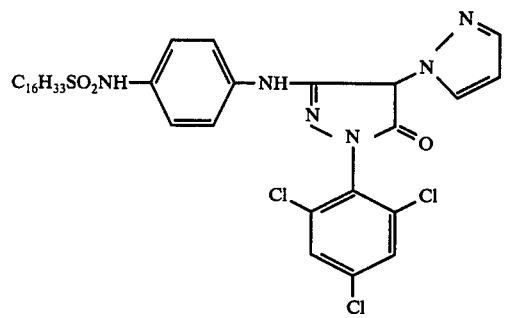
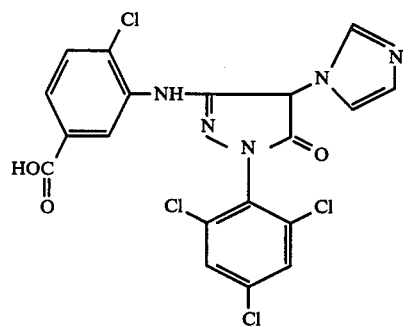
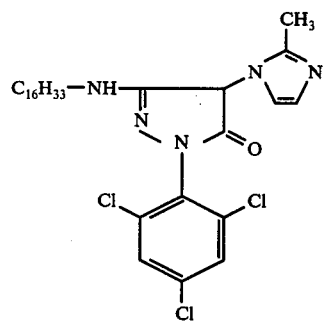

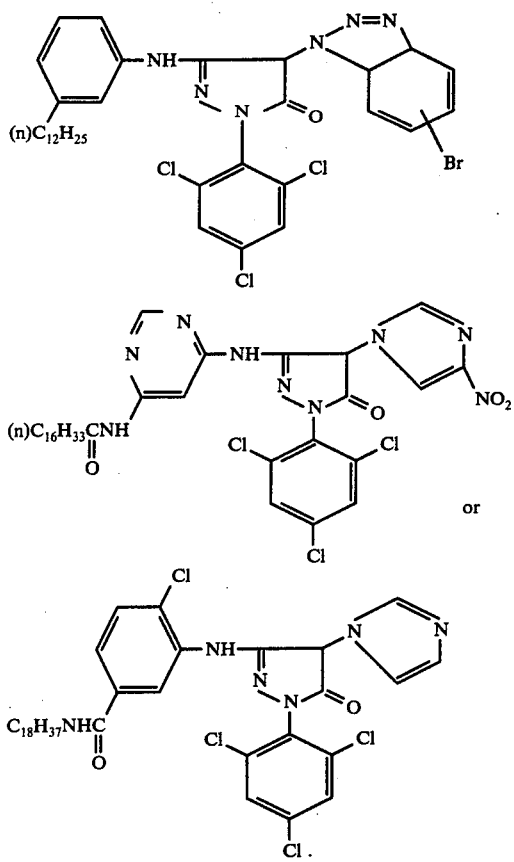
* * * * *